United States Patent
Tat et al.

(10) Patent No.: US 11,448,497 B2
(45) Date of Patent: Sep. 20, 2022

(54) SYSTEMS AND METHODS OF DETERMINING IMAGE SCALING

(71) Applicant: The Boeing Company, Chicago, IL (US)

(72) Inventors: Hong H. Tat, Redmond, WA (US); Brian T. Miller, Auburn, WA (US); Jason Wu, Sammamish, WA (US); Christina I. Fraij, Chicago, IL (US); Michael J. Schaffer, Olympia, WA (US); Kerth J. Downs, Auburn, WA (US); Grant C. Zenkner, Chicago, IL (US); Wayne A. Berry, Puyallup, WA (US)

(73) Assignee: The Boeing Company, Chicago, IL (US)

( * ) Notice: Subject to any disclaimer, the term of this patent is extended or adjusted under 35 U.S.C. 154(b) by 127 days.

(21) Appl. No.: 16/719,664

(22) Filed: Dec. 18, 2019

(65) Prior Publication Data

US 2021/0190489 A1 Jun. 24, 2021

(51) Int. Cl.
*G01B 11/14* (2006.01)
*G01C 11/30* (2006.01)
(Continued)

(52) U.S. Cl.
CPC .............. *G01B 11/14* (2013.01); *G01C 11/30* (2013.01); *H04N 17/002* (2013.01);
(Continued)

(58) Field of Classification Search
CPC ........ H04N 2005/2255; A61B 5/02156; A61B 5/1495; A61B 1/00057
See application file for complete search history.

(56) References Cited

U.S. PATENT DOCUMENTS 2,189,285 A * 2/1940 Gruber ................. G03B 23/105
359/467
4,549,207 A * 10/1985 Boshier .................. G01B 11/14
348/141
(Continued)

FOREIGN PATENT DOCUMENTS

CN 108 613 986 A 10/2018

OTHER PUBLICATIONS

S. Pulwer, P. Steglich, C. Villringer, J. Bauer, M. Burger, M. Franz, K. Grieshober, F. Wirth, J. Blondau, J. Rautenberg, S. Mouti, & S. Schrader, "Triangulation-based 3D surveying borescope", 9890 Proc. SPIE 091-096 (Apr. 26, 2016) (Year: 2016).*
(Continued)

*Primary Examiner* — David N Werner
(74) *Attorney, Agent, or Firm* — McDonnell Boehnen Hulbert & Berghoff LLP (57) ABSTRACT

An example system includes two objects each having a known dimension and positioned spaced apart by a known distance, and a fixture having an opening for receiving an imaging device and for holding the two objects in a field of view of the imaging device such that the field of view of the imaging device originates from a point normal to a surface of the base. The fixture holds the imaging device at a fixed distance from an object being imaged and controls an amount of incident light on the imaging device. An example method of determining image scaling includes holding an imaging device at a fixed distance from an object being imaged, and positioning the two objects in the field of view of the imaging device such that the field of view of the imaging device originates from a point normal to a line formed by the known distance.

20 Claims, 9 Drawing Sheets

(51) Int. Cl.
*H04N 17/00* (2006.01)
*A61B 5/0215* (2006.01)
*H04N 5/225* (2006.01)
*A61B 5/1495* (2006.01)
*A61B 1/00* (2006.01)

(52) U.S. Cl.
CPC ....... *A61B 1/00057* (2013.01); *A61B 5/02156* (2013.01); *A61B 5/1495* (2013.01); *H04N 2005/2255* (2013.01)

(56) References Cited

U.S. PATENT DOCUMENTS

| | | | | |
|---|---|---|---|---|
| 5,142,359 | A * | 8/1992 | Yamamori | A61B 1/042 348/70 |
| 5,148,502 | A * | 9/1992 | Tsujiuchi | H04N 5/262 348/E5.051 |
| 5,674,182 | A * | 10/1997 | Suzuki | A61B 1/121 600/129 |
| 5,820,547 | A * | 10/1998 | Strobl | H04N 17/002 600/117 |
| 6,361,490 | B1 * | 3/2002 | Irion | A61N 5/062 600/175 |
| 6,807,876 | B2 * | 10/2004 | Beck | A61B 5/1495 73/865.9 |
| 8,586,946 | B2 * | 11/2013 | Beck | A61B 5/1495 250/459.1 |
| 9,595,092 | B2 | 3/2017 | Wu et al. | |
| 9,934,564 | B2 | 4/2018 | Tat et al. | |
| 2003/0107726 | A1 * | 6/2003 | Hirt | A61B 1/00057 356/73.1 |
| 2005/0049457 | A1 * | 3/2005 | Leiner | G01M 11/00 600/117 |
| 2008/0228031 | A1 * | 9/2008 | Leiner | G01J 1/04 600/109 |
| 2010/0048993 | A1 * | 2/2010 | Shidara | A61B 1/04 600/109 |
| 2010/0110444 | A1 * | 5/2010 | Kuramoto | G01B 11/14 356/498 |
| 2010/0317919 | A1 * | 12/2010 | Takaoka | A61B 1/043 600/104 |
| 2011/0057930 | A1 * | 3/2011 | Keller | G06T 7/521 345/419 |
| 2011/0149057 | A1 * | 6/2011 | Beck | A61B 1/00057 348/E7.085 |
| 2014/0285676 | A1 * | 9/2014 | Barreto | H04N 17/002 348/187 |
| 2015/0346115 | A1 * | 12/2015 | Seibel | H04N 5/2256 348/50 |
| 2015/0348320 | A1 * | 12/2015 | Pesach | A61B 1/247 382/128 |
| 2017/0212066 | A1 | 7/2017 | Thompson et al. | |
| 2018/0007346 | A1 * | 1/2018 | Ushijima | A61B 1/00039 |
| 2019/0231220 | A1 * | 8/2019 | Refai | G06T 7/557 |
| 2019/0300135 | A1 * | 10/2019 | Troy | G03B 17/48 |

OTHER PUBLICATIONS

F. Inanc, A Borescope Based Optical Surface Scanner, 894 AIP Conf. Proc. 1715-1722 (Mar. 2007) (Year: 2007).*
E.B. Hubben & D. Jervis, "Advances in Three Dimensional Measurement in Remote Visual Inspection", presented at 18 World Conf. on Nondestructive Testing (Apr. 2012) (Year: 2012).*
European Search Report prepared by the European Patent Office in Application No. EP 20 19 6534.0 dated Mar. 25, 2021.

* cited by examiner

SYSTEMS AND METHODS OF DETERMINING IMAGE SCALING

FIELD

The present disclosure relates generally to fixtures for holding an imaging device, and systems and methods for determining image scaling, for example.

BACKGROUND

Many aircraft or other vehicle components are increasingly being fabricated from composite materials. At least some structures fabricated from composite materials may undergo nondestructive evaluation and/or inspection prior to installation and/or use to ensure that irregularities, such as wrinkles, have not formed during fabrication that may affect and/or alter a mechanical property of the composite material.

On aircraft, for example, there is a need for detection and/or measurement of wrinkles along cut edges of at least some components manufactured from composite materials. A "wrinkle," as the term is used herein, refers generally to an irregularity such as a ply distortion in a composite material. In one example, to measure wrinkles along the cut edges of components, the edge of a cut part is highly polished and placed on a flatbed scanner to capture cross-sectional images of the cut part for analysis. In another method, such images are captured using a hand held portable ultra-violet (UV) microscope. The latter method is time intensive and prone to variability (e.g., in scale, incident lighting, etc.) between scan locations and inspectors. The images are generally manually scaled and light-corrected before algorithms can be used for analysis on the images.

What is needed is a system that enables images to be captured in manner that is repeatable and has less variability in results.

SUMMARY

In an example, a fixture is described comprising a hollow elongate section having a first end and a second end, and the first end has an opening for receiving a lens portion of an imaging device and the second end is structurally configured to brace against a surface of an object being imaged. The hollow elongate section is configured to hold the lens portion of the imaging device at a fixed distance from an object being imaged as well as to control an amount of incident light on the lens portion of the imaging device.

In another example, a system is described comprising an imaging device, a calibration object, and a fixture having an opening for receiving a lens portion of the imaging device and for holding the calibration object in a field of view of the imaging device. The fixture holds the imaging device at a fixed distance from an object being imaged as well as controls an amount of incident light on the imaging device.

In another example, a method of configuring an imaging device for capturing images of an object is described comprising holding, via a fixture, a lens portion of an imaging device at a fixed distance from an object being imaged, controlling an amount of incident light on the lens portion of the imaging device by use of the fixture, and holding, via the fixture, a calibration object in a field of view of the imaging device.

In another example, a system is described comprising two objects each having a known dimension and positioned on a base spaced apart by a known distance, and a fixture having an opening for receiving a lens portion of an imaging device and for holding the two objects in a field of view of the imaging device such that the field of view of the imaging device originates from a point normal to a surface of the base. The fixture holds the imaging device at a fixed distance from an object being imaged as well as controls an amount of incident light on the imaging device.

In another example, a method of configuring an imaging device for capturing images of an object is described comprising holding an imaging device at a fixed distance, by a fixture, from an object being imaged, holding two objects in a field of view of the imaging device, and the two objects each have a known dimension and are positioned to be spaced apart by a known distance, and positioning the two objects in the field of view of the imaging device such that the field of view of the imaging device originates from a point normal to a line formed by the known distance between the two objects.

In another example, a method of determining physical measurements of wrinkles in a composite component is described comprising positioning a lens portion of an imaging device into a first end of a fixture, and the fixture controls an amount of incident light on the imaging device and holds a calibration object in a field of view of the imaging device. The method also comprises placing the imaging device at a fixed distance from a cross-section of a composite component being imaged, and the fixture includes a flat distal portion for abutting an edge of the object to be imaged and the fixed distance is based on a length of the flat distal portion. The method also comprises causing the imaging device to capture an image of the cross-section of the composite component with the calibration object in the image, determining an image scaling factor that associates a number of pixels in the image to a physical distance based on a known dimension of the calibration object, and determining physical measurements of wrinkles in the composite component using the image scaling factor.

In another example, a system is described comprising a base, two objects each having a known dimension and positioned on the base spaced apart by a known distance, an imaging device positioned such that the two objects are in a field of view of the imaging device and such that the field of view of the imaging device originates from a point normal to a surface of the base, and a computing device having one or more processors and non-transitory computer readable medium storing instructions, that when executed by the one or more processors, causes the computing device to perform functions. The functions include receiving an image from the imaging device capturing the two objects in the field of view, and based on one or more of the known dimension of the two objects and the known distance between the two objects, determining an image scaling factor that associates a number of pixels in the image to a physical distance.

In another example, a method of determining image scaling is described comprising capturing an image by an imaging device that includes two objects in a field of view of the imaging device, and the two objects each have a known dimension and are positioned on a base spaced apart by a known distance, and based on the known dimension of the two objects and the known distance between the two objects, determining an image scaling factor that associates a number of pixels in the image to a physical distance.

In another example, a non-transitory computer readable medium storing instructions, that when executed by a computing device having one or more processors causes the computing device to perform functions is described. The functions comprise capturing an image by an imaging device that includes two objects in a field of view of the imaging device, and the two objects each have a known dimension and are positioned on a base spaced apart by a known distance, and based on the known dimension of the two objects and the known distance between the two objects, determining an image scaling factor that associates a number of pixels in the image to a physical distance.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Within examples, automated systems and methods are described for performing image scaling. In an example, an object is placed in a field of view of a camera or microscope to allow for calculation of the physical scaling of the captured image.

Image scaling is useful in many instances. An example includes verification of manufactured components. One verification method includes measurements of wrinkles in composite parts. Performing wrinkle measurements typically requires cut-edges of parts to be highly polished for physical scanning on large machines, such as to capture a cross-sectional image to allow analysis of the individual plies in that section of the composite part, or manual measurements and/or imaging are required. However, manual processes can be subject to variability and are time consuming.

Using examples described herein, a fixture holds an imaging device (e.g., camera or microscope) to shield the imaging device from incident light and provide constant distance to the object being imaged, which reduces both the time and variability of the measurements. Furthermore, calibration objects are included with the holder to enable calculation of an image scaling factor so as to generate the physical measurements from the images. For example, to make physical measurements from an image, the physical spacing for each pixel in the image is needed. The examples described herein solves a problem of providing a physical artifact to be placed in the field of view of the camera that will be captured in the image and can be analyzed to determine the scaling.

The example systems and methods reduce an amount of time required to perform measurements and also improve a quality of the measurements due to less variability. The fixture thus enables reliable and repeatable data for image scaling to be calculated.

Figures 1, 2, 3, 4:
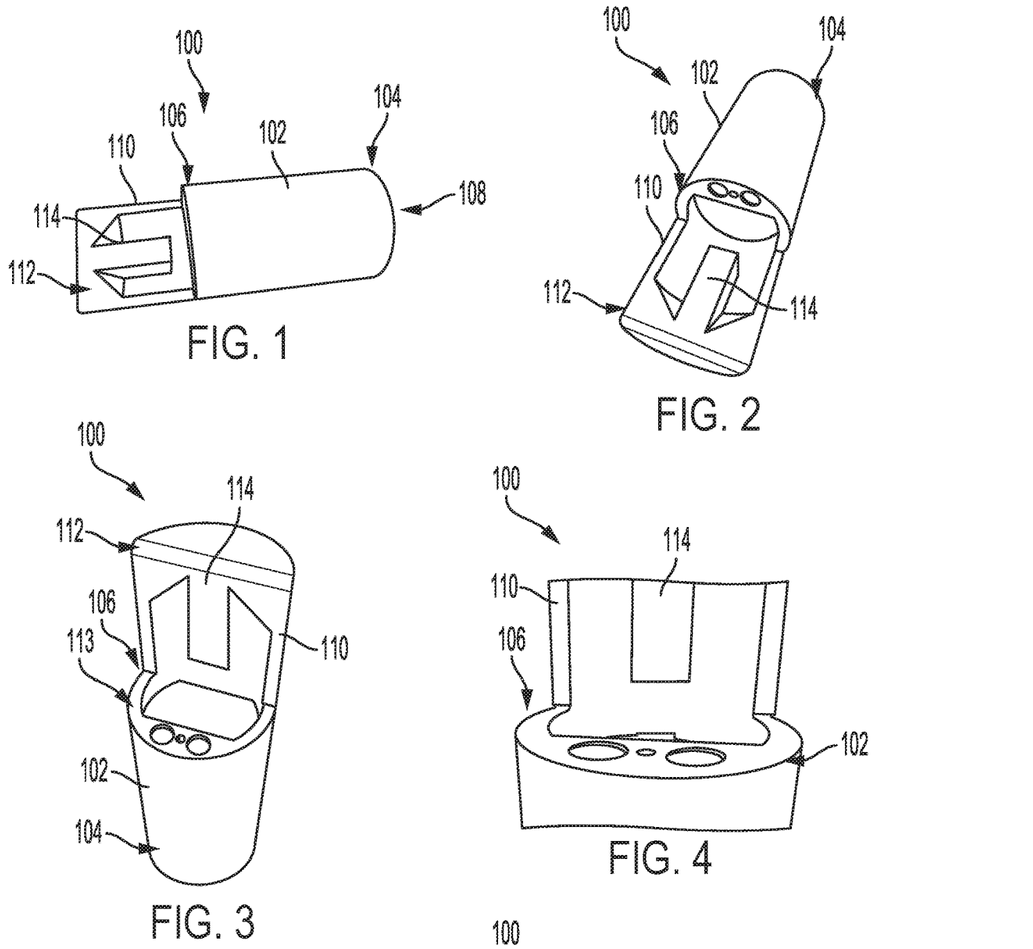
FIG. 1 illustrates a bottom view of a fixture, according to an example implementation.
FIG. 2 illustrates a perspective view of the fixture, according to an example implementation.
FIG. 3 illustrates a front view of the fixture, according to an example implementation.
FIG. 4 illustrates a magnified view of a portion of the fixture, according to an example implementation.
Figure 5:
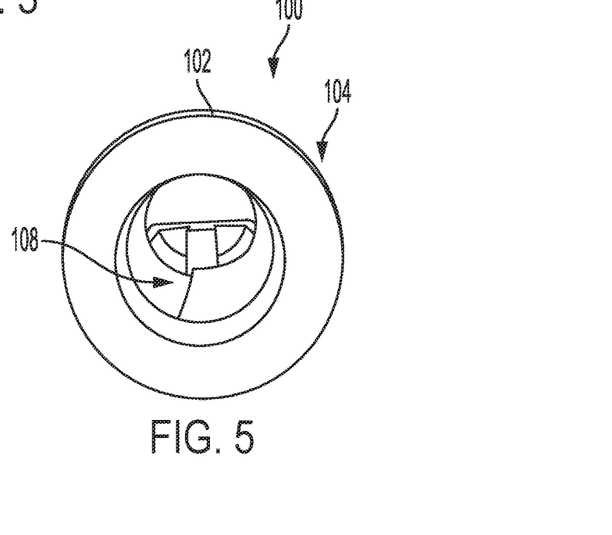
FIG. 5 illustrates a back view of the fixture, according to an example implementation.

Referring now to the figures, FIGS. 1-5 illustrate an example of a fixture 100, according to an example implementation. FIG. 1 illustrates a bottom view of the fixture 100, FIG. 2 illustrates a perspective view of the fixture 100, FIG. 3 illustrates a front view of the fixture 100, FIG. 4 illustrates a magnified view of a portion of the fixture 100, and FIG. 5 illustrates a back view of the fixture 100.

The fixture 100 includes a hollow elongate section 102 having a first end 104 and a second end 106, and the first end 104 has an opening 108 for receiving a lens portion of an imaging device (shown in FIGS. 12-15) and the second end 106 is structurally configured to brace against a surface of an object being imaged. The hollow elongate section 102 is configured to hold the lens portion of the imaging device at a fixed distance from an object being imaged as well as to control an amount of incident light on the lens portion of the imaging device.

The fixture 100 may be comprised of any suitable material, such as a rubber or plastic material, and can be manufactured using additive manufacturing processes, for example.

The hollow elongate section 102 is shown as a cylindrical portion and an internal area of the hollow elongate section 102 is open. The opening 108 for receiving the lens portion of the imaging device is disposed at the first end 104. The second end 106 is structurally configured to brace against a surface of an object being imaged, such as by having an end surface that is flat.

The fixture 100 also includes an extension section 110 connected to the second end 106 of the hollow elongate section 102, and the extension section 110 is configured to brace the hollow elongate section 102 along an edge of the object being imaged and to maintain the hollow elongate section 102 level with respect to the edge of the object being imaged. To do so, for example, the extension section 108 has a flat surface 112 for seating on the edge of the object being imaged. For example, the extension section 110 of the fixture 100 has a flat distal portion for abutting an edge of the object to be imaged.

Additionally, the extension section 110 is connected to the second end 106 of the hollow elongate section 102 at a seat 113, as shown in FIG. 3, and the seat 113 contacts the surface of the object being imaged.

The extension section 110 may include a half-circular portion of the cylindrical portion of the hollow elongate section 102. Thus, half of the cylinder of a cylindrically-shaped extension section can be considered to have been cut-out, and what remains is the extension section 110. Within examples, the hollow elongate section 102 and the extension section 110 are one integral component. In other examples, the hollow elongate section 102 and the extension section 110 may be separate components coupled together.

The extension section 110 includes an internal structure 114 arranged lengthwise along the extension section 110, such as for holding a calibration object (not shown in FIGS. 7-11) adjacent to the second end 106 of the hollow elongate section 102, and thus in view of a lens portion of an imaging device positioned at opening 108. The internal structure 114 and the extension section 110 are shown as one integral component in the illustrated embodiment, and the extension section 110 is hollowed out in areas to create the internal structure 114.

Figure 6A:
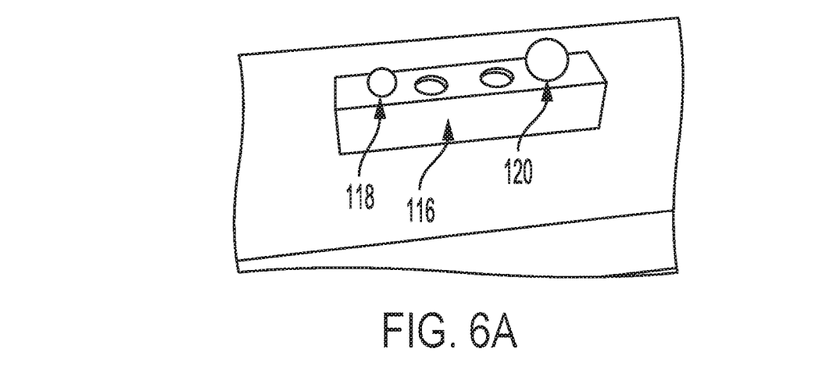
FIG. 6A illustrates an example of a base including two calibration objects, according to an example implementation.
Figure 6B:
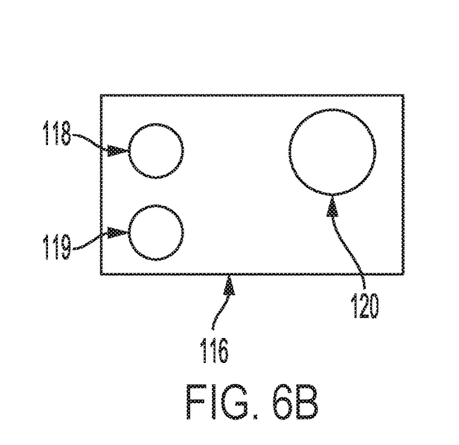
FIG. 6B illustrates an additional example of the base with a different configuration of calibration objects, according to an example implementation.
Figure 6C:
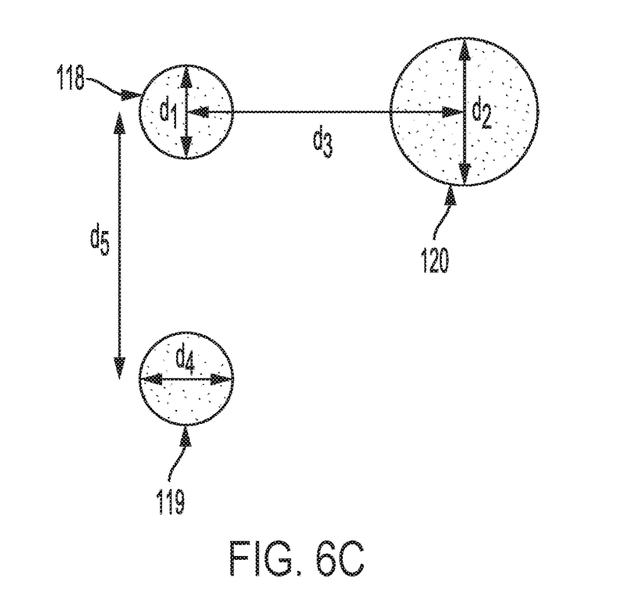
FIG. 6C illustrates an additional example of the base with dimensions of the configuration of calibration objects, according to an example implementation.
Figure 7:
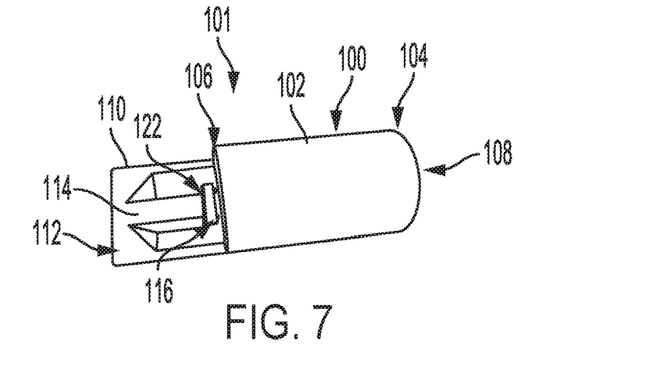
FIG. 7 illustrates a bottom view of the fixture with the base, according to an example implementation.
Figure 8:
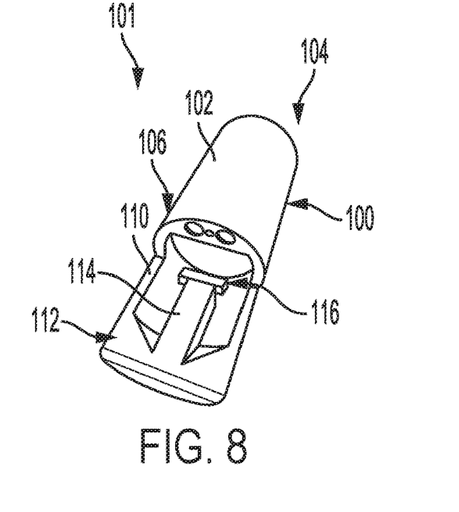
FIG. 8 illustrates a perspective view of the fixture with the base, according to an example implementation.
Figure 9:
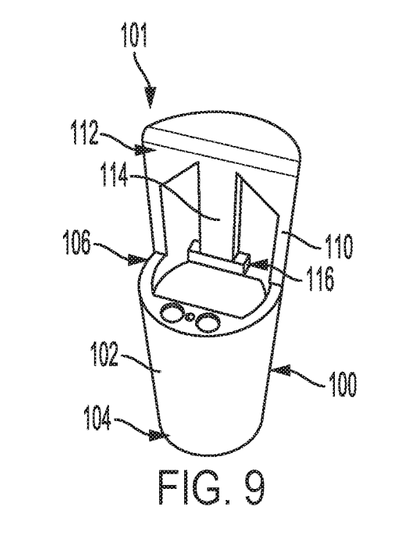
FIG. 9 illustrates a front view of the fixture with the base, according to an example implementation.
Figure 10:
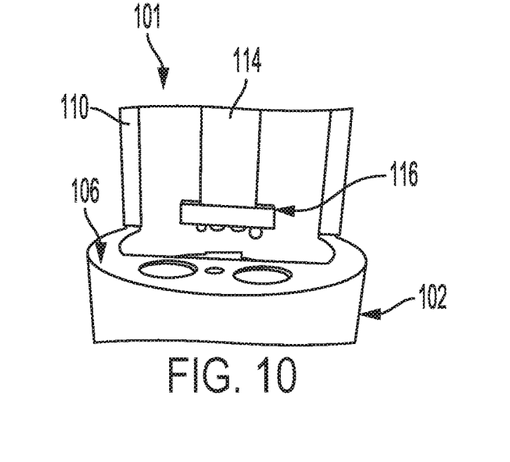
FIG. 10 illustrates a magnified view of a portion of the fixture with the base, according to an example implementation.
Figure 11:
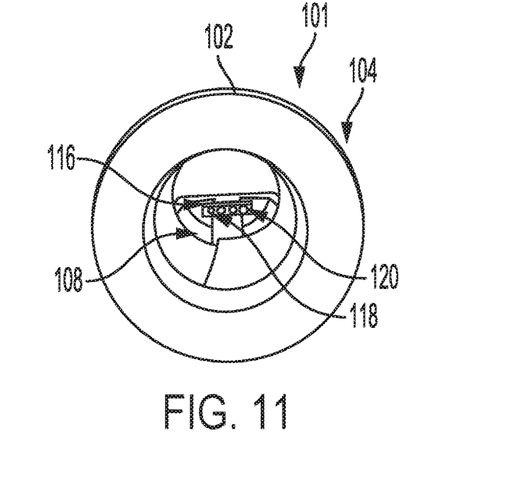
FIG. 11 illustrates a back view of the fixture with the base, according to an example implementation.

Fixture 100 can thus be used with a variety of configurations of calibration objects. FIG. 6A illustrates an example of a base 116 including two calibration objects 118 and 120. FIGS. 6B-6C illustrate additional examples of the base 116 with a different configuration of calibration objects. FIGS. 7-11 illustrate the base 116 installed within the fixture 100. Namely, FIG. 7 illustrates a bottom view of the fixture 100 with the base 116, FIG. 8 illustrates a perspective view of the fixture 100 with the base 116, FIG. 9 illustrates a front view of the fixture 100 with the base 116, FIG. 10 illustrates a magnified view of a portion of the fixture 100 with the base 116, and FIG. 11 illustrates a back view of the fixture 100 with the base 116.

In FIGS. 7-11, the base 116 is coupled to an end 122 of the internal structure 114, and the calibration objects 118 and 120 are positioned on the base 116. For example, the base 116 is coupled to an underside surface of the extension section 110 such that the calibration objects 118 and 120 are positioned at substantially the same distance from the lens portion of the imaging device as a surface of the object being imaged (shown in FIGS. 13-15). As described more fully below, the calibration objects 118 and 120 each have a known diameter and are spaced apart by a known distance, such that when the calibration objects 118 and 120 are placed in the field of view of an imaging device, the calibration objects 118 and 120 can be used as a basis to determine a scale of the image during image processing. A distance parameter can be calculated, which is self-checked against the known diameters of the calibration objects 118 and 120, for example.

In one example, the fixture 100 with the base 116 is considered a system 101, as shown in FIG. 7. The system 101 includes two objects (e.g., calibration objects 118 and 120) each having a known dimension and positioned on the base 116 spaced apart by a known distance. The fixture 100 has the opening 108 for receiving a lens portion of an imaging device and for holding the two objects in a field of view of the imaging device such that the field of view of the imaging device originates from a point normal to a surface of the base 116, and the fixture 100 holds the imaging device at a fixed distance from an object being imaged as well as controls an amount of incident light on the imaging device. More details are described below with respect to FIGS. 12-15.

Referring back to FIG. 6A, in one example, the two calibration objects 118 and 120 each comprise a disc-shape, and the two calibration objects have different dimensions. The extension section 110 is connected to the second end 106 of the hollow elongate section 102, and includes the internal structure 114 arranged lengthwise along the extension section 110 for holding the two calibration objects 118 and 120 adjacent to the second end 106 of the hollow elongate section 102.

The two calibration objects 118 and 120 can each include a circular cross-section and the known dimensions of the two calibration objects 118 and 120 is a diameter of the circular cross-section. In some examples, at least one of the two calibration objects 118 and 120 includes a sphere-shaped object. Further, such as to assist a viewer or an image-processing program in discerning the edge of the calibration object, at least one of the two calibration objects 118 and 120 includes a substantially solid color. Thus, the two calibration objects 118 and 120 can include spherical objects of a substantially solid color.

Referring to FIG. 6B, the base 116 can, in some embodiments, further include a third object 119 positioned on the base 116 such that the two objects 118 and 120 and the third object 119 form a triangle, and distances between vertices of the triangle are known distances. For example, as shown in FIG. 6C, the two objects 118 and 120 have known diameters of $d_1$ and $d_2$, respectively, and are separated by a known distance $d_3$. The third object 119 has a known diameter $d_4$ and is separated from the object 118 by a known distance $d_5$. A distance between object 119 and object 120 is also known as well (e.g., $\sqrt{(d_5^2+d_3^2)}$). These distances and diameters can be used to determine an image scaling factor during image processing, as described below.

Figure 12:
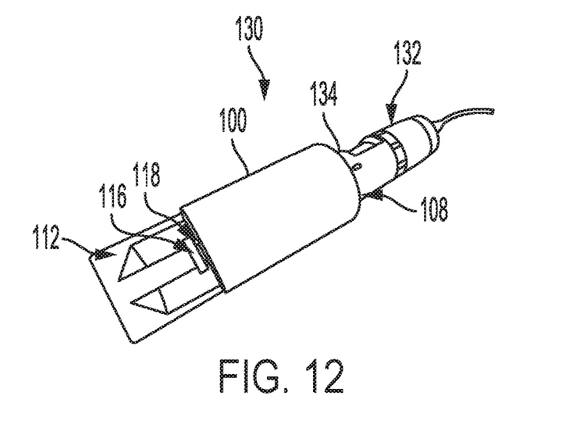
FIG. 12 illustrates an example of a system, according to an example implementation.

Referring now to FIG. 12, an example of a system 130 is illustrated, according to an example implementation. The system 130 includes an imaging device 132, the calibration object 118, and the fixture 100 having the opening 108 for receiving a lens portion 134 of the imaging device 132 and for holding the calibration object 118 in a field of view of the imaging device 132. The fixture 100 holds the imaging device 132 at a fixed distance from an object being imaged as well as controls an amount of incident light on the imaging device 132.

As shown in FIG. 12, the lens portion 134 of the imaging device 132 can be snap fit into the opening 108 and an opposite end includes a cord. In one example, the imaging device 132 connects to a computing device via the cord (shown in FIG. 13).

In one example, the imaging device 132 includes an ultraviolet microscope. The fixture 100 holds the imaging device 132 (such as a UV microscope) at a fixed distance from a cut edge of a composite piece and controls the incident light on the imaging device 132 so that the imaging device 132 can produce digital images that may be more easily processed by known measurement algorithms, such as algorithms described in U.S. Pat. No. 9,595,092. The fixture 100 also holds the calibration object 118 in the field of view of the imaging device 132 to enable automated calculation of image scale (e.g., photogrammetry target dot). Although only one calibration object is described in this example, more than one calibration object may be used in other examples.

As with the examples shown in earlier figures, in FIG. 12, the fixture 100 is shown to have a flat distal portion (e.g., flat surface 112) for abutting an edge of the object being imaged.

Figure 13:
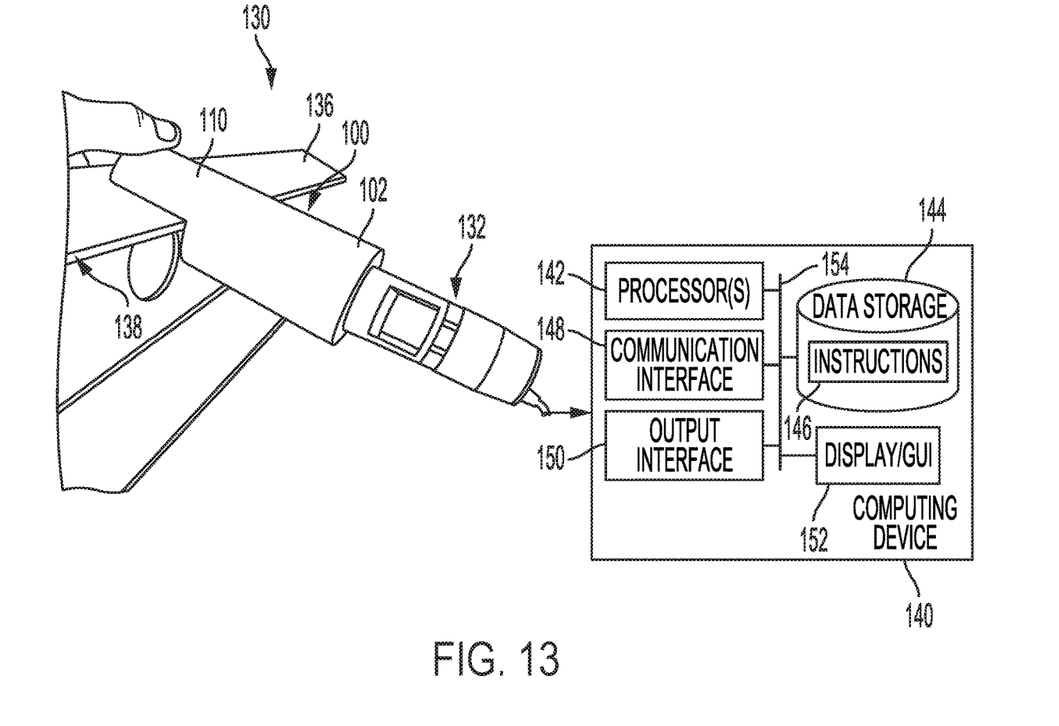
FIG. 13 illustrates an example of the system being used to capture images of an object, according to an example implementation.

FIG. 13 illustrates an example of the system 130 being used to capture images of an object 136, according to an example implementation. In this example, the fixture 100 is placed against the object to capture an image of a cross-section 138 of the object 136. The underside of the extension section 110 sits on top of a surface of the object 136, and the seat 113 (shown in FIG. 3) abuts a surface of the cross-section 138 of the object 136. The fixture 100 thus holds the imaging device 132 at a constant distance from the object 136 at all times during imaging.

In operation, the imaging device 132 is used to image the cross-section 138 of the object 136 along a full length of the object 136. Thus, an operator will manually move the imaging device 132 lengthwise along the object 136 and the fixture 100 maintains the distance between the surface of the cross-section 138 of the object 136 and the imaging device 132 at a constant distance during imaging of the cross-section 138. The images are then processed to calculate measurements of components used in manufacturing the object 136.

In one example, to facilitate processing of the images, as shown in FIG. 13, the system 130 also includes a computing device 140 coupled to the imaging device 132 and having one or more processors 142 and non-transitory computer readable medium (e.g., data storage 144) storing instructions 146, that when executed by the one or more processors 142, causes the computing device 140 to perform functions. The functions include receiving an image from the imaging device 132 capturing a cross-section of a composite component with the calibration object 118 in the image, calculating an image scaling factor using known dimensions of the calibration object 118, and determining a physical measurement of a wrinkle in the composite component using the image scaling factor. More details of the image processing are described below with reference to FIGS. 18-21.

The computing device 140 is shown as a stand-alone component in FIG. 13. In some other examples, the computing device 140 may be included within the imaging device 132 as well.

To perform image processing functions, the computing device 140 includes the processors 142, the data storage 144, a communication interface 148, an output interface 150, a display/graphical user interface (GUI) 152, and each component of the computing device 140 is connected to a communication bus 154. The computing device 140 may also include hardware to enable communication within the computing device 140 and between the computing device 140 and other devices (not shown). The hardware may include transmitters, receivers, and antennas, for example.

The communication interface 148 may be a wireless interface and/or one or more wireline interfaces that allow for both short-range communication and long-range communication to one or more networks or to one or more remote devices. Such wireless interfaces may provide for communication under one or more wireless communication protocols, Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. Thus, the communication interface 190 may be configured to receive input data from one or more devices, and may also be configured to send output data to other devices.

The data storage 144 may include or take the form of memory, such as one or more computer-readable storage media that can be read or accessed by the one or more processor(s) 142. The computer-readable storage media can include volatile and/or non-volatile storage components, such as optical, magnetic, organic or other memory or disc storage, which can be integrated in whole or in part with the one or more processor(s) 142. The data storage 144 is considered non-transitory data storage or non-transitory computer readable media. In some examples, the data storage 144 can be implemented using a single physical device (e.g., one optical, magnetic, organic or other memory or disc storage unit), while in other examples, the non-transitory data storage 144 can be implemented using two or more physical devices.

The data storage 144 thus is a computer readable medium, and instructions 146 are stored thereon. The instructions 146 include computer executable code.

The one or more processor(s) 142 may be general-purpose processors or special purpose processors (e.g., digital signal processors, application specific integrated circuits, etc.). The one or more processor(s) 142 may receive inputs from the communication interface 148 as well as from other sensors, and process the inputs to generate outputs that are stored in the data storage 144. The one or more processor(s) 142 can be configured to execute the instructions 146 (e.g., computer-readable program instructions) that are stored in the data storage 144 and are executable to provide the functionality of the computing device 140 described herein.

The output interface 150 outputs information for reporting or storage, and thus, the output interface 150 may be similar to the communication interface 148 and can be a wireless interface (e.g., transmitter) or a wired interface as well.

The display 152 may include a touchscreen or other display configured to provide a GUI. In some examples, the processor 142 can execute the instructions 146 to perform functions including receiving live video from the imaging device 132, and displaying the live video on the GUI. Following, the functions can also include enabling capture of an image within the live video, and then causing a wrinkle measurement to be performed on the image. The wrinkle measurement can be made of a cross-section of the object that was imaged, for example.

Figure 14:
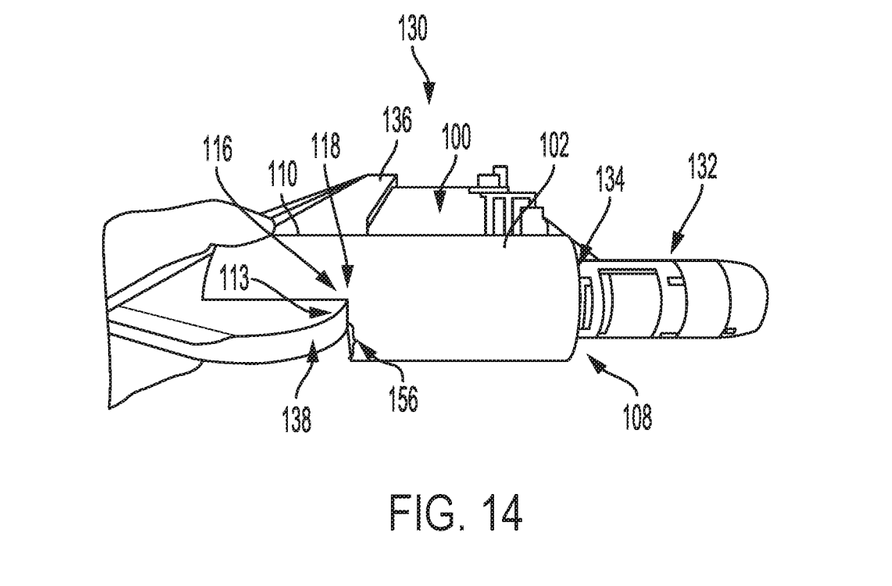
FIG. 14 illustrates side view of the system being used to capture images of the object, according to an example implementation.
Figure 15:
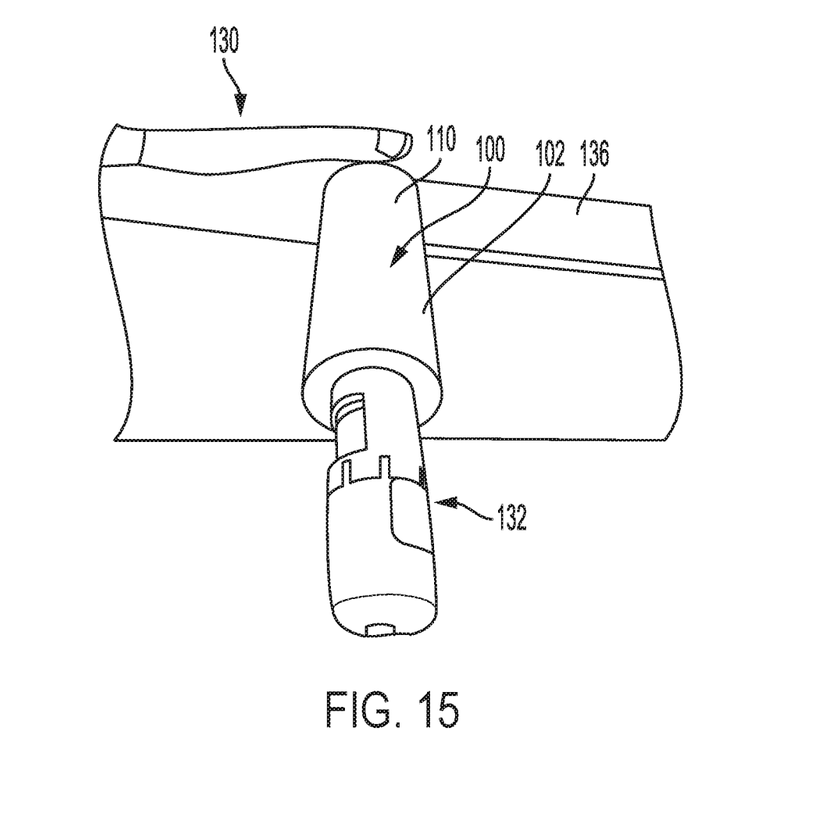
FIG. 15 illustrates a top view of the system being used to capture images of the object, according to an example implementation.

FIG. 14 illustrates side view of the system 130 being used to capture images of the object 136, according to an example implementation. FIG. 15 illustrates a top view of the system 130 being used to capture images of the object 136, according to an example implementation.

Figure 16:
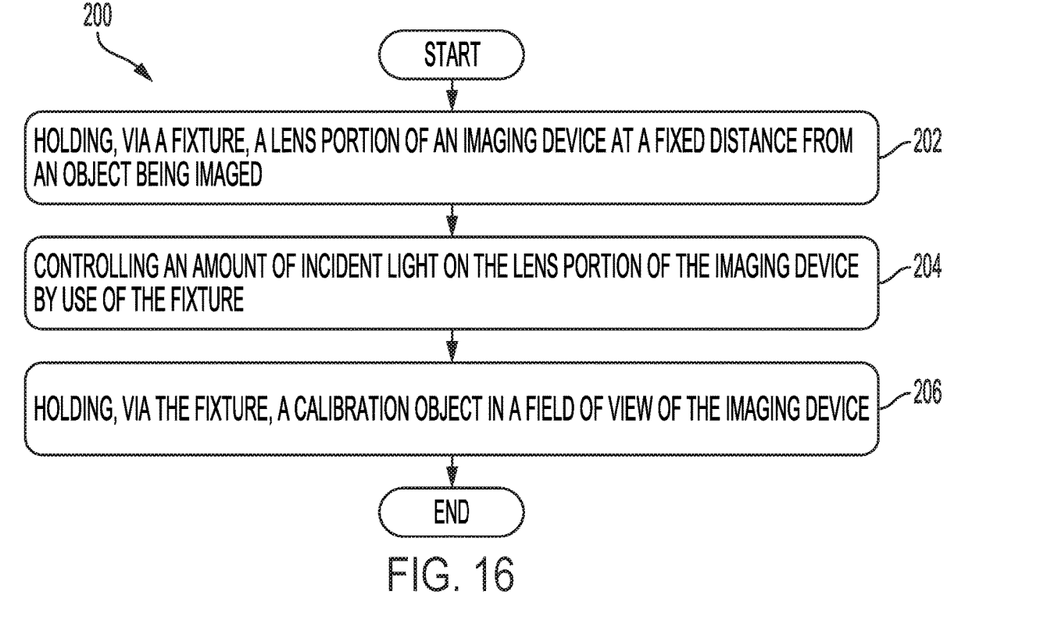
FIG. 16 shows a flowchart of an example of a method of configuring the imaging device for capturing images of the object, according to an example implementation.

FIG. 16 shows a flowchart of an example of a method 200 of configuring the imaging device 132 for capturing images of the object 136, according to an example implementation. Method 200 shown in FIG. 16 presents an example of a method that could be used with the system 130, for example. With all methods described herein, devices or systems may be used or configured to perform logical functions presented in the methods. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 200 may include one or more operations, functions, or actions as illustrated by one or more of blocks 202-206. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. Alternative implementations are included within the scope of the examples of the present disclosure in which functions may be executed out of order from that shown or discussed, including substantially concurrent or in reverse order, depending on the functionality involved, as would be understood by those reasonably skilled in the art.

Description of the method 200 is provided below with reference to FIGS. 12-16.

Initially, as shown at block 202, the method 200 includes holding, via the fixture 100, the lens portion 134 of the imaging device 132 at a fixed distance from the object 136 being imaged. As described above, the seat 113 of the hollow elongate section 102 will contact a surface of the cross-section 138 of the object 136 being imaged. The extension section 110 also contacts a top surface of the object 136 being imaged. Thus, the fixture 100 holds the imaging device 132 at the fixed distance from the object 136.

As shown at block 204, the method 200 includes controlling an amount of incident light on the lens portion 134 of the imaging device 132 by use of the fixture 100. For example, since the lens portion 134 is inserted into the opening 108 and into an interior of the hollow elongate section 102, the lens portion 134 will be shielded from light coming from a direction of the opening 108 because there is no clearance for light to enter through the opening 108 once the lens portion 134 is inserted. Therefore, the only light that may be incident on the lens portion 134 is via an opening at the second end 106 or at the seat 113, for example. However, due to the configuration of the seat 113 as well as to the configuration of the extension section 110, a minimal amount of light may be incident upon the lens portion 134. Furthermore, once the seat 113 contacts the surface of the cross-section 138 of the object 136 being imaged, less light will be incident upon the lens portion 134. In FIG. 14, an area 156 is shown by which light may be incident on the lens portion 134, for example.

As shown at block 206, the method 200 includes holding, via the fixture 100, the calibration object 118 in a field of view of the imaging device 132. Block 206 can include positioning the base 116 to an underside surface of the fixture 100, and positioning the calibration object 118 on the base 116. In FIG. 14, the base 116 and the calibration object 118 are conceptually shown with dotted lines to provide a perspective of a location of the components internal to the extension section 110 and the hollow elongate section 102.

In one example, block 206 further includes positioning the calibration object 118 at substantially the same distance from the lens portion 134 of the imaging device 132 as a surface of the object 136 being imaged. Thus, the distance to the calibration object 118 and the lens portion 134 and the distance to the surface of the cross-section 138 and the lens portion 134 is substantially the same.

In a further example, the object 136 being imaged comprises a composite component, and the method 200 further includes receiving an image from the imaging device 132 capturing a cross-section of the composite component with the calibration object 118 in the image, calculating an image scaling factor using known dimensions of the calibration object 118, and determining a physical measurement of a wrinkle in the composite component using the image scaling factor. More details of these functions are described below with reference to FIGS. 18-21.

Figure 17:
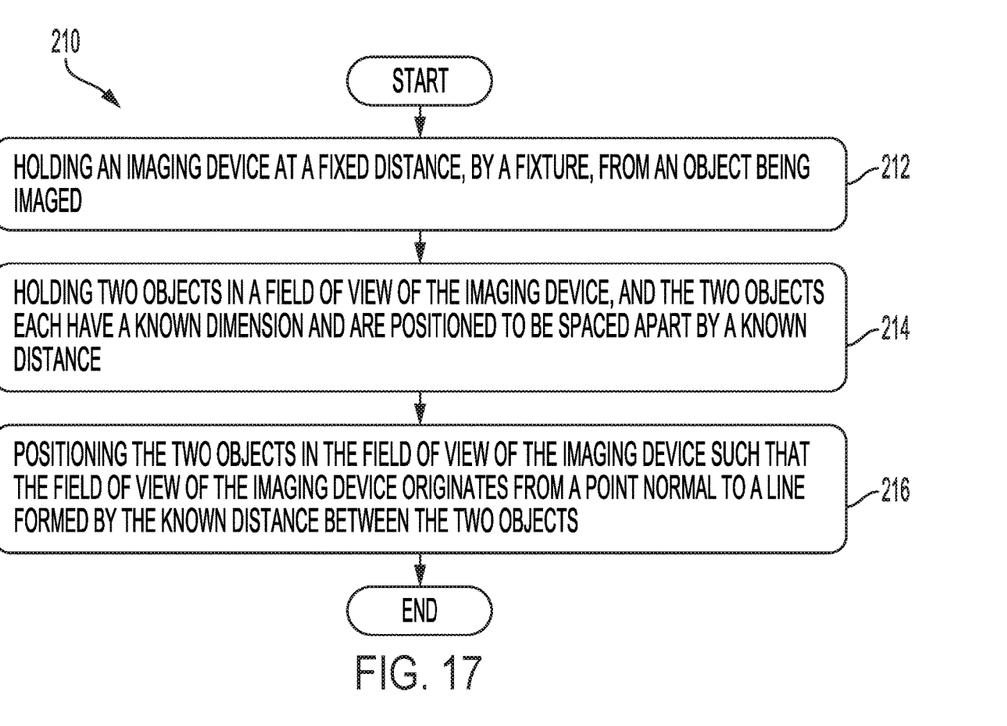
FIG. 17 shows a flowchart of an example of another method of configuring the imaging device for capturing images of the object, according to an example implementation.

FIG. 17 shows a flowchart of an example of another method 210 of configuring the imaging device 132 for capturing images of the object 136, according to an example implementation. Method 210 shown in FIG. 17 presents an example of a method that could be used with the system 130, for example. Method 210 may include one or more operations, functions, or actions as illustrated by one or more of blocks 212-216. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

As shown at block 212, the method 210 includes holding the imaging device 132 at a fixed distance, by the fixture 100, from the object 136 being imaged.

As shown at block 214, the method 210 includes holding two objects 118 and 120 in a field of view of the imaging device 132, and the two objects 118 and 120 each have a known dimension and are positioned to be spaced apart by a known distance. For example, the fixture 100 has the opening 108 for receiving a lens portion of the imaging device 132 and for holding the two objects 118 and 120 in a field of view of the imaging device 132. In addition, the fixture 100 includes the extension section 110 connected to the second end 106 of the hollow elongate section 102, and the block 214 can include holding the two objects 118 and 120 on the base 116 coupled to the extension section 110 and positioned at substantially the same distance from the lens portion 134 of the imaging device 132 as a surface of the object 136 being imaged.

As shown at block 216, the method 210 includes positioning the two objects 118 and 120 in the field of view of the imaging device 132 such that the field of view of the imaging device 132 originates from a point normal to a line formed by the known distance between the two objects 118 and 120.

Figure 18:
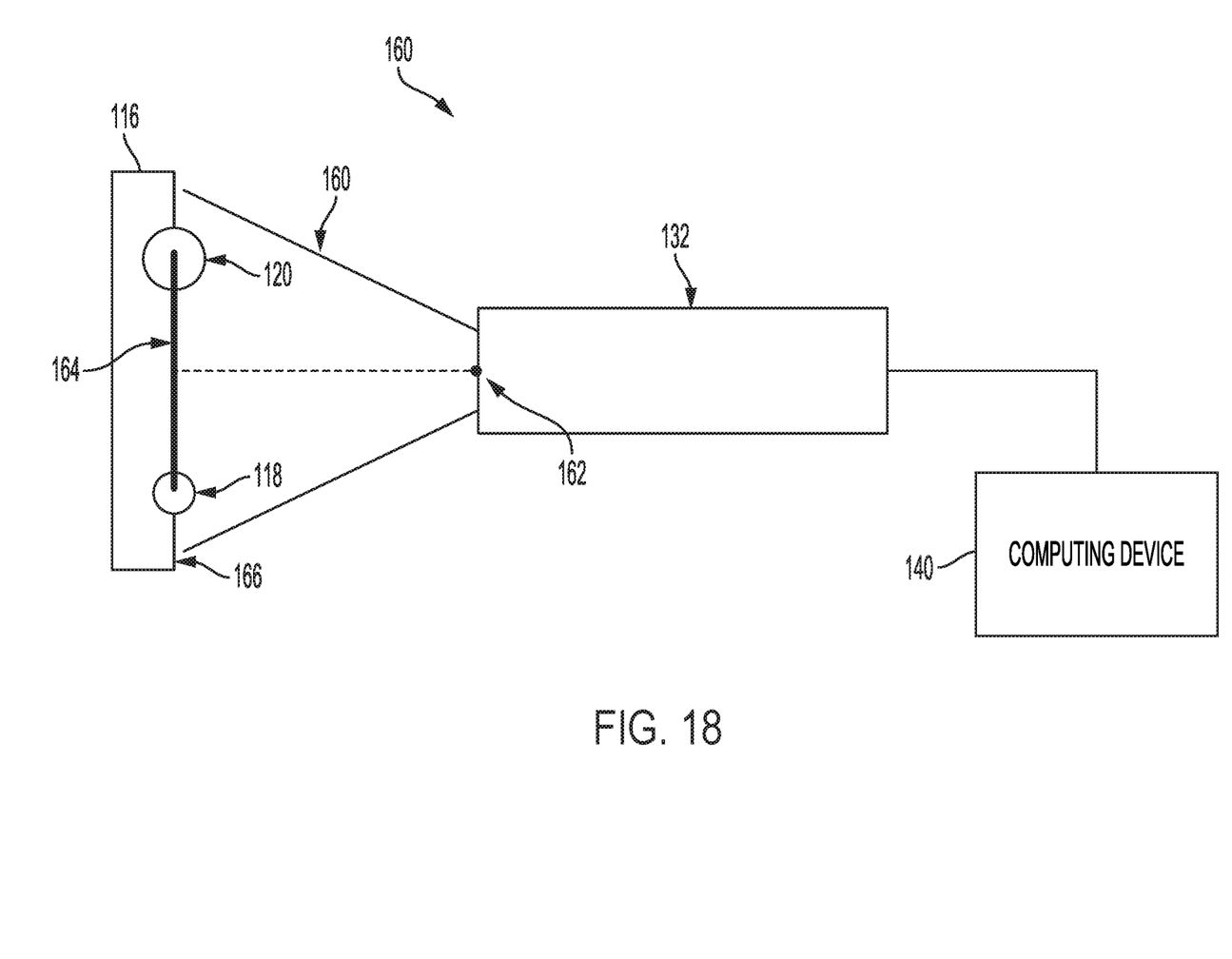
FIG. 18 illustrates an example of a system including a configuration of the imaging device with respect to the two objects, according to an example implementation.

FIG. 18 illustrates an example of a system 160 including a configuration of the imaging device 132 with respect to the two objects 118 and 120, according to an example implementation. As mentioned at block 216 of the method 210, the fixture 100 (not shown in FIG. 18) holds the two objects 118 and 120 in a field of view 161 of the imaging device 132 such that the field of view 161 of the imaging device 132 originates from a point 162 normal to a line 164 formed by the known distance between the two objects 118 and 120. The point 162 is also normal to a surface 166 of the base 116. In one example, the point 162 normal to the surface 166 of the base 116 is also equidistant from a center of both of the two objects 118 and 120.

Referring back to the method 210 in FIG. 17, in further examples, the method 210 includes controlling an amount of incident light on the lens portion 134 of the imaging device 132 by use of the fixture 100, and holding a lens portion 134 of the imaging device 132 in an opening disposed at the first end of the fixture 100.

Within examples, when imaging the object 136, the method 210 may additionally include positioning a flat distal portion of the fixture 100 abutting an edge of the object 136 to be imaged, and the fixed distance is based on a length of the flat distal portion. Imaging the object can further include bracing against a surface of the object 136 being imaged via the second end of the fixture contacting the surface of the object 136 being imaged.

In further examples, the method 210 can also include holding a third object 119 in the field of view 161 of the imaging device 132, and the two objects 118 and 120 and the third object 119 are positioned such that the two objects 118 and 120 and the third object 119 form a triangle and distances between vertices of the triangle are known distances.

Turning again to FIG. 18, the system 160 illustrates the base 116, the two objects 118 and 120 each having a known dimension and positioned on the base 116 spaced apart by a known distance, the imaging device 132 positioned such that the two objects 118 and 120 are in the field of view 161 of the imaging device 132 and such that the field of view 161 of the imaging device 132 originates from the point 162 normal to the surface 166 of the base 116, and the computing device 140 coupled to the imaging device 132. The computing device 140 has one or more processors 142 and non-transitory computer readable medium (e.g., data storage 144) storing instructions 146, that when executed by the one or more processors 142, causes the computing device 140 to perform functions of receiving an image from the imaging device 132 capturing the two objects 118 and 120 in the field of view 161, and based on one or more of the known dimension of the two objects 118 and 120 and the known distance between the two objects 118 and 120, determining an image scaling factor that associates a number of pixels in the image to a physical distance.

Figure 19:
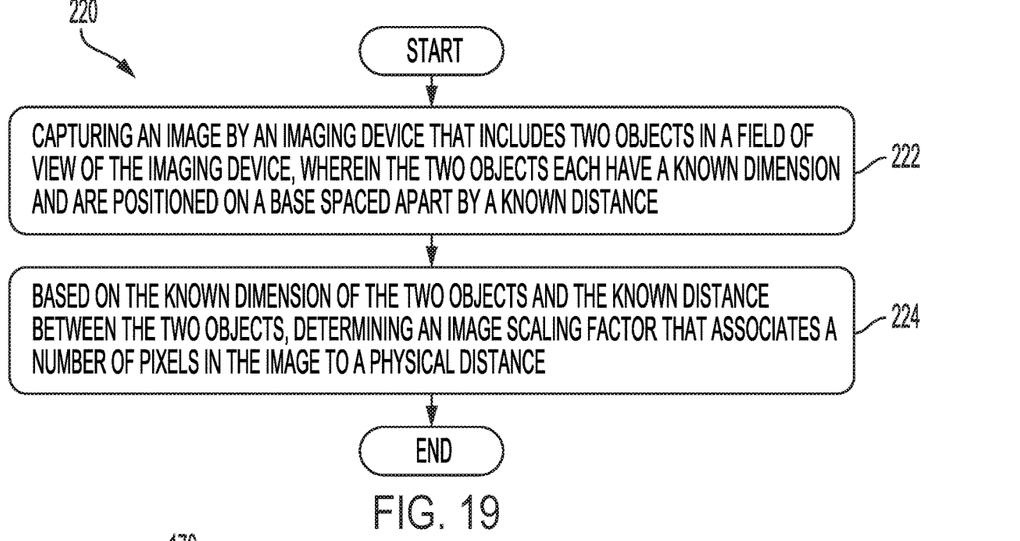
FIG. 19 shows a flowchart of an example of a method of determining image scaling, according to an example implementation.

FIG. 19 shows a flowchart of an example of a method 220 of determining image scaling, according to an example implementation. Method 220 shown in FIG. 19 presents an example of a method that could be used with the system 130 shown in FIG. 13 or with the system 160 shown in FIG. 18, for example. Method 220 may include one or more operations, functions, or actions as illustrated by one or more of blocks 222-224. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 19, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 222, the method 220 includes capturing an image by the imaging device 132 that includes two objects 118 and 120 in a field of view 161 of the imaging device 132, and the two objects 118 and 120 each have a known dimension and are positioned on a base spaced apart by a known distance.

At block 224, the method 220 includes based on the known dimension of the two objects 118 and 120 and the known distance between the two objects 118 and 120, determining an image scaling factor that associates a number of pixels in the image to a physical distance. In one example, block 224 includes determining the number of pixels between approximate center positions of the two objects 118 and 120 in the image, and then associating the number of pixels with the known distance. The physical distance between the two objects 118 and 120 may be a center to center distance and since this physical distance is known, e.g., 0.02 inch, then the number of pixels between center positions of the two objects 118 and 120 in the image is associated with the known distance to provide a measurement indicating a distance per pixel. Then, associating the number of pixels with the known distance includes dividing the number of pixels by the known distance to generate the image scaling factor in a form of distance per pixel.

In some examples, the method 220 also includes thresholding the image to determine a location of pixels along an edge of the two objects 118 and 120, identifying an approximate center of the two objects 118 and 120 using the location of pixels along the edge of the two objects, and determining an amount of pixels between the approximate center of the two objects 118 and 120 to be the number of pixels.

Figure 20:
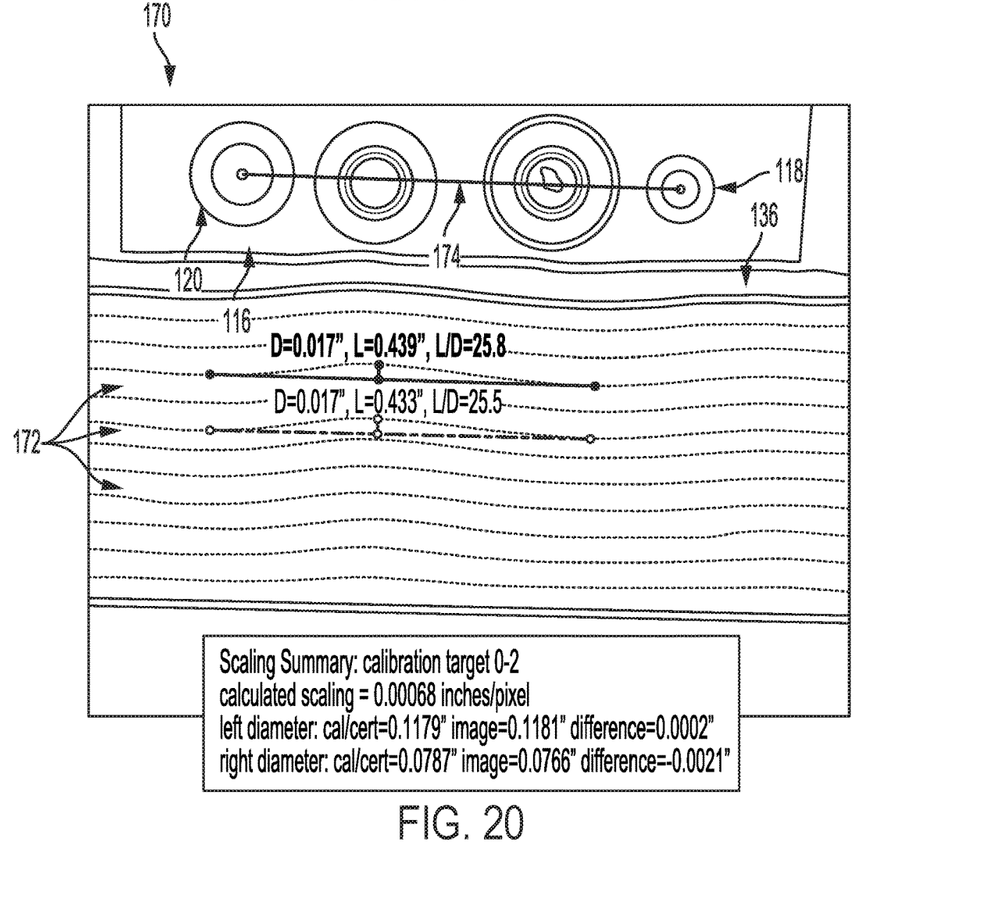
FIG. 20 illustrates an example of an image captured by the imaging device, according to an example implementation.

FIG. 20 illustrates an example of an image 170 captured by the imaging device 132 and includes post-processing, according to an example implementation. In this example, the object 136 being imaged is a composite component comprised of multiple layers of plies 172 stacked on top of each other. The image 170 specifically is of a cross-section of the composite component, and used to measure dimensions of wrinkles along a cut edge of the composite component. As an example, wrinkles or non-straight plies, can occur in composite components, and there is a need for measurement of wrinkles along cut edges of certain components of vehicles. The imaging device 132 can thus capture the image 170, and physical distances or measurements of wrinkles can be determined using the image scaling factor that is determined.

With the acquired image, the two objects 118 and 120 are detected by thresholding the image and locating pixels along an edge of the two objects 118 and 120. Thresholding can be accomplished with the two objects being a robust color, such as red, to identify a change in pixel color for location of an outline of the objects 118 and 120. With the pixels on the edge of the two objects 118 and 120 identified, a radius and center (in terms of pixels) of each of the two objects 118 and 120 is calculated. A distance in pixels between the centers of the two objects 118 and 120 is calculated (e.g., shown by line 174 in FIG. 20) and is divided by the known physical distance between the two objects 118 and 120. The result is spacing (e.g., inches/pixel) for each pixel in the image 170. Using the calculated spacing value, the radius/diameter of each of the two objects 118 and 120 identified via image processing can be compared to the known physical dimensions of the two objects 118 and 120 to serve as a check Thus, in one example, returning to FIG. 19, the method 220 can also include performing a self-check of the image scaling factor using the known dimension of at least one of the two objects 118 and 120. FIG. 20 illustrates an example in which the imaging scaling factor is calculated as 0.00068 inches/pixel (text is super-imposed on the image to provide details). For the object 120, the known dimension is 0.1179 inches and the image processed dimension is 0.1181 inches (using the imaging scaling factor). This results in a difference of 0.0002 inches, which is an acceptable tolerance. For the object 118, the known dimension is 0.0787 inches and the image processed dimension is 0.0766 inches (using the imaging scaling factor). This results in a difference of 0.0021 inches, which is an acceptable tolerance. Thus, the self-check is complete and the calculations have been verified.

Following, the wrinkle measurements can be performed. FIG. 20 illustrates an example in which a length (L) of a first wrinkle, using the image scaling factor, is determined to be 0.439 inches at a depth (D) of 0.017 inches for L/D of 25.8. A length of a second wrinkle is determined to be 0.433 inches at a depth of 0.017 inches for L/D of 25.5. Returning to FIG. 19, the method 220 may thus additionally include capturing the image of a cross-section of a composite component, and determining a physical measurement of a wrinkle in the composite component using the image scaling factor. This additional function can include finding the multiple layers of plies 172 first so as to generate the lines between wrinkles, for example.

In another example, the method 220 may additionally include for at least one of the two objects 118 and 120, determining a second number of pixels along a length of a dimension of the at least one of the two objects 118 and 120, using the image scaling factor to convert the second number of pixels into a distance, and based on comparing the distance with the known distance of the at least one of the two objects, outputting an error result. In this example, a diameter of one of the objects 118 and 120 can be used for a further comparison, and when the known diameter varies from the image processed calculated diameter (e.g., using the image scaling factor and pixel measurement), an error result is output. The error may be the result of poor lighting or camera movement, and can indicate to capture a new image.

In another example, the two objects 118 and 120 can have different dimensions, and the method 220 may include performing a self-check of the image scaling factor using the known dimension of both of the two objects 118 and 120 to provide two additional measurements for calibration. Thus, calculations of the image processed diameters of each of the two objects 118 and 120 (e.g., using the image scaling factor and pixel measurements) can be performed and compared to the known diameter values for further self-check processes because once the pixel spacing is found from the center to center distance, the image scaling factor can be used to compare any dimension as measured from the image to the known dimension. Thus, two different diameters of the two objects 118 and 120 provides two additional measurements for calibration.

In an example where three objects are used, as shown in FIG. 6B, image scaling can be provided along two different dimensions in the image. Thus, the method 220 may additionally include determining the image scaling factor along a first direction (such as shown in FIG. 20 as horizontal), based on the respective known distance between one of the two objects 118 and 120 and the third object 119, determining a second image scaling factor along a second direction that associates a second number of pixels in the image to a second physical distance. The second direction may be vertical, such as between the objects 118 and 119, as shown in FIG. 6C.

Figure 21:
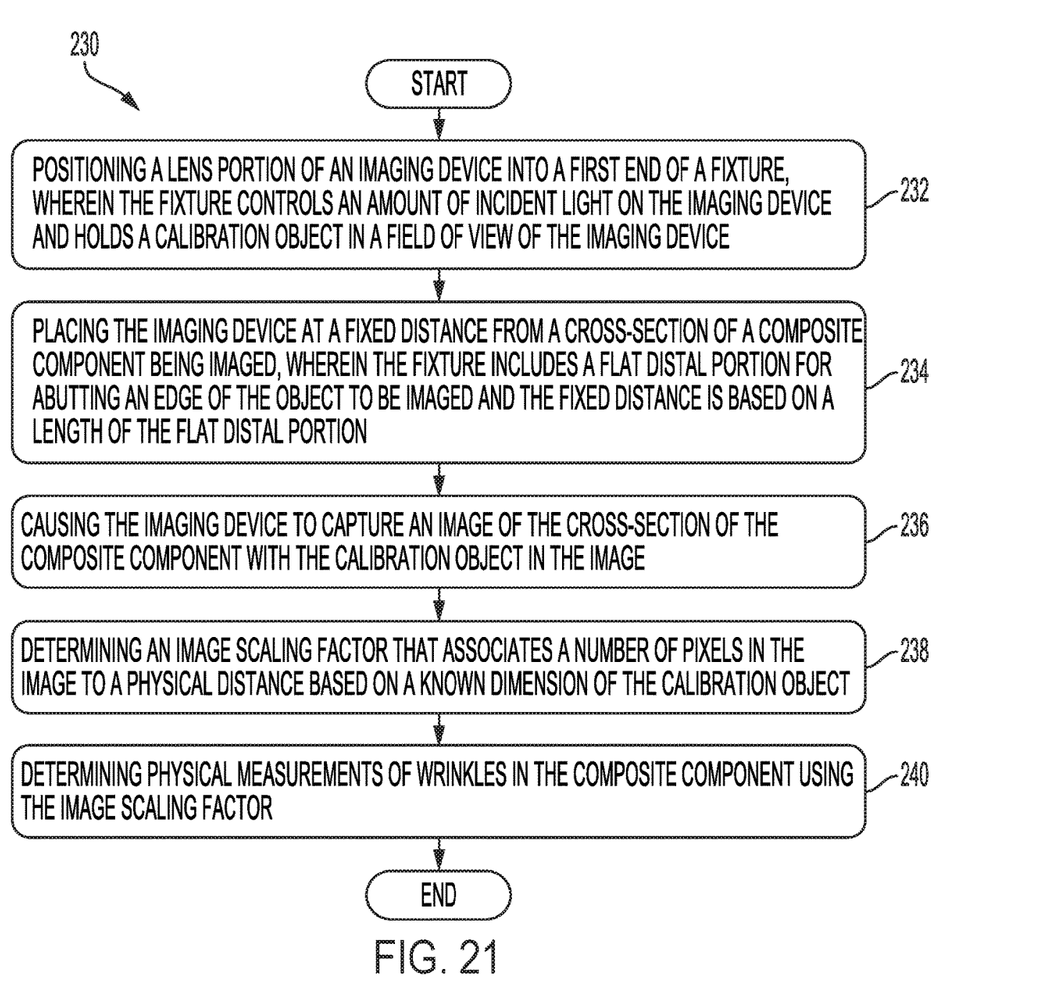
FIG. 21 shows a flowchart of an example of a method of determining physical measurements of wrinkles in a composite component, according to an example implementation.

FIG. 21 shows a flowchart of an example of a method 230 of determining physical measurements of wrinkles in a composite component, according to an example implementation. Method 230 shown in FIG. 21 presents an example of a method that could be used with the system 130 shown in FIG. 13 or with the system 160 shown in FIG. 18, for example. Method 230 may include one or more operations, functions, or actions as illustrated by one or more of blocks 232-240. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 232, the method 230 includes positioning a lens portion 134 of an imaging device 132 into a first end 104 of a fixture 100, and the fixture 100 controls an amount of incident light on the imaging device 132 and holds a calibration object in a field of view 161 of the imaging device 132. At block 234, the method 230 includes placing the imaging device 132 at a fixed distance from a cross-section of a composite component being imaged, and the fixture 100 includes a flat distal portion for abutting an edge of the object to be imaged and the fixed distance is based on a length of the flat distal portion. At block 236, the method 230 includes causing the imaging device to capture an image of the cross-section of the composite component with the calibration object in the image. The computing device 140 may be programmed to trigger image capture of the image, for example. At block 238, the method 230 includes determining an image scaling factor that associates a number of pixels in the image to a physical distance based on a known dimension of the calibration object. At block 240, the method 230 includes determining physical measurements of wrinkles in the composite component using the image scaling factor.

In one example, the calibration object 118 is a first object and is positioned on a base 116 coupled to the fixture, and the method 230 further includes positioning a second object 120 on the base 116, and the first object 118 and the second object 120 are positioned on the base 116 spaced apart by a known distance, and causing the image device to capture the image with the first object 118 and the second object 120 in the field of view 161. The method 230 may further include determining the number of pixels between approximate center positions of the first object 118 and the second object 120, and associating the number of pixels with the known distance.

In some examples, the method 230 includes performing a self-check of the image scaling factor using the known dimension the first object 118.

In some additional examples, the method 230 includes positioning a third object 119 on the base 116 such that the first object 118, the second object 120, and the third object 119 form a triangle, and distances between vertices of the triangle are known distances. The method 230 may then include causing the image device to capture the image with the first object 118, the second object 120, and the third object 119 in the field of view 161 and the image scaling factor is determined along a first direction. The method 230 may then include based on the respective known distance between one of the first and second objects 118 and 120 and the third object 119, determining a second image scaling factor along a second direction that associates a second number of pixels in the image to a second physical distance.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A system comprising:
   two objects, comprising a first object and a second object, each having a known dimension and positioned on a base spaced apart by a known distance; and
   a fixture having an opening for receiving a lens portion of an imaging device and for holding the two objects in a field of view of the imaging device such that the field of view of the imaging device originates from a point normal to a surface of the base, wherein the fixture holds the imaging device at a fixed distance from a component being imaged as well as controls an amount of incident light on the imaging device,
   wherein the fixture comprises:
   a hollow elongate section having a first end and a second end, wherein the opening for receiving the lens portion of the imaging device is disposed at the first end and the second end is structurally configured to brace against a surface of the component being imaged;
   an extension section connected to the second end of the hollow elongate section, the extension section including an internal structure arranged lengthwise along the extension section for holding the two objects adjacent to the second end of the hollow elongate section, wherein the extension section has a flat distal portion extending lengthwise for abutting an edge of the component to be imaged.

2. The system of claim 1, wherein the two objects each comprise a disc-shape.

3. The system of claim 1, wherein at least one of the two objects comprises a spherical-shape.

4. The system of claim 1, wherein the two objects have different dimensions.

5. The system of claim 1, further comprising:
   a third object positioned on the base such that the two objects and the third object form a triangle, and distances between vertices of the triangle are known distances.

6. The system of claim 5, further comprising:
   a computing device having one or more processors and non-transitory computer readable medium storing instructions, that when executed by the one or more processors, causes the computing device to perform functions of:
   receiving an image capturing the two objects and the third object in the field of view;
   determining an image scaling along a first direction, wherein the image scaling factor associates a number of pixels in the image to a physical distance; and
   based on the respective known distance between one of the two objects and the third object, determining a second image scaling factor along a second direction that associates a second number of pixels in the image to a second physical distance.

7. The system of claim 1, further comprising:
   a computing device having one or more processors and non-transitory computer readable medium storing instructions, that when executed by the one or more processors, causes the computing device to perform functions of:
   receiving an image from the imaging device capturing the two objects in the field of view; and
   based on one or more of the known dimension of the two objects and the known distance between the two objects, determining an image scaling factor that associates a number of pixels in the image to a physical distance.

8. The system of claim 7, wherein determining the image scaling factor that associates the number of pixels to the physical distance comprises:
   determining the number of pixels between approximate center positions of the two objects; and
   associating the number of pixels with the known distance.

9. The system of claim 7, wherein the two objects have different dimensions, and wherein the functions further comprise:
   performing a self-check of the image scaling factor using the known dimensions of both of the two objects to provide two additional measurements for calibration.

10. A method of configuring an imaging device for capturing images of an object, comprising:
   holding an imaging device at a fixed distance, by a fixture, from a component being imaged, wherein the fixture has a hollow elongate section having a first end and a second end, and an extension section connected to the second end of the hollow elongate section, and wherein a lens portion of the imaging device is positioned in an opening disposed at the first end;
   holding two objects in a field of view of the imaging device, and the two objects each have a known dimension and are positioned to be spaced apart by a known distance, wherein the two objects are positioned on a base coupled to the extension section and positioned at substantially the same distance from the lens portion of the imaging device as a surface of the component being imaged;
   positioning a flat distal portion of the extension section extending lengthwise abutting an edge of the component to be imaged, and the fixed distance is based on a length of the flat distal portion; and
   positioning the two objects in the field of view of the imaging device such that the field of view of the imaging device originates from a point normal to a line formed by the known distance between the two objects.

11. The method of claim 10, further comprising:
   controlling an amount of incident light on the lens portion of the imaging device by use of the fixture.

12. The method of claim 10, further comprising:
   bracing against a surface of the component being imaged via the second end contacting the surface of the component being imaged.

13. The method of claim 10, further comprising:
   holding a third object in the field of view of the imaging device, and the two objects and the third object are positioned such that the two objects and the third object form a triangle and distances between vertices of the triangle are known distances.

14. The method of claim 10, wherein holding the two objects in the field of view of the imaging device comprises holding the two objects that each comprise a disc-shape.

15. The method of claim 10, wherein holding the two objects in the field of view of the imaging device comprises holding at least one of the two objects that comprises a spherical-shape.

16. The method of claim 10, wherein holding the two objects in the field of view of the imaging device comprises holding the two objects that each have different dimensions.

17. A method of determining physical measurements of wrinkles in a composite component, the method comprising:
   positioning a lens portion of an imaging device into a first end of a fixture, wherein the fixture controls an amount of incident light on the imaging device and holds a calibration object in a field of view of the imaging device;
   placing the imaging device at a fixed distance from a cross-section of a composite component being imaged, wherein the fixture includes a flat distal portion for abutting an edge of the object to be imaged and the fixed distance is based on a length of the flat distal portion;
   causing the imaging device to capture an image of the cross-section of the composite component with the calibration object in the image;
   determining an image scaling factor that associates a number of pixels in the image to a physical distance based on a known dimension of the calibration object; and
   determining physical measurements of wrinkles in the composite component using the image scaling factor.

18. The method of claim 17, wherein the calibration object is a first object and is positioned on a base coupled to the fixture, and the method further comprises:
   positioning a second object on the base, wherein the first object and the second object are positioned on the base spaced apart by a known distance;
   wherein causing the imaging device to capture the image of the cross-section of the composite component comprises causing the image device to capture the image with the first object and the second object in the field of view;
   wherein determining the image scaling factor that associates the number of pixels in the image to the physical distance comprises:
      determining the number of pixels between approximate center positions of the first object and the second object; and
      associating the number of pixels with the known distance.

19. The method of claim 17, further comprising:
   performing a self-check of the image scaling factor using the known dimension the first object.

20. The method of claim 17, further comprising:
   positioning a third object on the base such that the first object, the second object, and the third object form a triangle, and distances between vertices of the triangle are known distances; and
   wherein causing the imaging device to capture the image of the cross-section of the composite component comprises causing the image device to capture the image with the first object, the second object, and the third object in the field of view;
   wherein determining the image scaling factor comprises determining the image scaling along a first direction; and
   wherein the functions further comprise:
      based on the respective known distance between one of the first and second objects and the third object, determining a second image scaling factor along a second direction that associates a second number of pixels in the image to a second physical distance.

* * * * *